United States Patent [19]

Miyamae et al.

[11] Patent Number: 4,558,707

[45] Date of Patent: Dec. 17, 1985

[54] ELECTRONIC SPHYGMOMANOMETER WITH VOICE SYNTHESIZER

[75] Inventors: Ryuichi Miyamae, Osaka; Haruo Yasuda, Yamatokoriyama, both of Japan

[73] Assignee: Sharp Kabushiki Kaisha, Osaka, Japan

[21] Appl. No.: 463,475

[22] Filed: Feb. 3, 1983

[30] Foreign Application Priority Data

Feb. 9, 1982 [JP] Japan .............................. 57-17285[U]
Feb. 9, 1982 [JP] Japan .............................. 57-17286[U]
Feb. 16, 1982 [JP] Japan .............................. 57-20860[U]

[51] Int. Cl.[4] .............................. A61B 5/02

[52] U.S. Cl. .............................. 128/683; 128/680; 381/53

[58] Field of Search .............................. 128/677, 680–683; 381/51, 53

[56] References Cited

U.S. PATENT DOCUMENTS

| | | | |
|---|---|---|---|
| Re. 28,529 | 8/1975 | Edenhofer | 128/701 |
| 3,550,582 | 12/1970 | Wilhelmson | 128/683 |
| 3,732,868 | 5/1973 | Willems et al. | 128/701 |
| 4,273,136 | 6/1981 | Kubo et al. | 128/681 X |
| 4,326,536 | 4/1982 | Kitagawa et al. | 128/682 |
| 4,429,367 | 1/1984 | Ikeda | 381/51 X |

*Primary Examiner*—Lee S. Cohen
*Assistant Examiner*—Angela D. Sykes
*Attorney, Agent, or Firm*—Birch, Stewart, Kolasch & Birch

[57] ABSTRACT

A sphygmomanometer comprises pressure detection elements for measuring an applied sphygmomanometeric pressure and providing an output indicative of the pressure, and a voice synthesizer responsive to the pressure detection elements for synthesizing voice indicative of the pressure and generating the voice.

9 Claims, 9 Drawing Figures

Limb 14
11 Cuff
19
Systolic/Diastolic Pressure Detector
5
21
25
2
22
Pressure-Reduction Detection CCT
20
Systolic/Diastolic Pressure Memory
Voice Control CCT
Voice CCT
Speaker
18
15
12
Pressure Sensor
Pressure Converter CCT
Pressure Hose
Pressure -Reduction Means
16
A
17
Comparator
A>B
28
26
Bulb
Predetermined Value Memory CCT
B
Adder
27
23
Pressure Value Memory CCT
13
Pressure Value Detection CCT
24

ELECTRONIC SPHYGMOMANOMETER WITH VOICE SYNTHESIZER

BACKGROUND OF THE INVENTION

The present invention relates to a blood pressure measuring instrument, i.e., a sphygmomanometer and, more particularly, to an electronic sphygmomanometer with a voice synthesizer for measuring and speaking patient's systolic and diastolic pressures.

Conventionally, a patient systolic blood pressure and diastolic blood pressure are measured using an inflatable occluding cuff which usually is wrapped about a patient's limb so as to close, or completely occlude, an artery. Typically, the occluding cuff is wrapped about the arm in juxtaposition to the brachial artery. When the cuff is inflated to a pressure which exceeds the patient's systolic pressure, so as to close this artery, blood is no longer capable of flowing therethrough. As the cuff is slowly deflated, a point is reached at which the patient's systolic pressure exceeds the cuff pressure. Consequently, the artery opens for a short period during the patient's cardiac cycle. Once the blood pressure during this cardiac cycle falls below the cuff pressure, the artery once again is closed.

The pressure in the cuff which is equal to the maximum blood pressure during a cardiac cycle is, of course, the systolic pressure. It is known that when the blood pressure exceeds the actual cuff pressure, resulting in the opening of the artery, turbulence in the blood stream is accompanied by a sound which is the so-called Korotkoff sound. These Korotkoff sounds occur each time the artery is opened. Thus, as long as the cuff pressure exceeds the lowest, or diastolic, pressure in the cardiac cycle, the artery will be alternately opened and closed as the cardiac cycle pressure traverses the cuff pressure. When the cuff pressure falls below the lowest pressure point in the cardiac cycle, the artery will remain opened, and the Korotkoff sounds no longer will be produced. Consequently, by measuring the cuff pressure at the last Korotkoff sound, a close approximation is made of the patient's diastolic pressure.

Conventionally, an operator must read the systolic and diastolic pressure displayed in a digital or analog display. Therefore, a blind man cannot operate the sphygmomanometer. Further, when an operator measures his blood pressure himself, his inexperience in reading these pressures may cause him to be confused so that his blood pressure may change when he reads these pressures.

Therefore, it is desired for the sphygmomanometer to speak the blood pressures.

SUMMARY OF THE INVENTION

Accordingly, it is an object of the present invention to provide an improved sphygmomanometer for speaking or audibly outputting blood pressures.

It is another object of the present invention to provide an improved sphygmomanometer for speaking systolic/diastolic pressures measured thereby.

It is a further object of the present invention to provide an improved sphygmomanometer for speaking blood pressures each time a pressure to inflate an occluding cuff increases over a predetermined value.

It is a further object of the present invention to provide an improved sphygmomanometer for speaking to inform an operator whether the sphygmomanometer can start a measurement operation.

Briefly described, in accordance with the present invention, a sphygmomanometer comprises pressure detection means for measuring an applied sphygmomanometeric pressure and providing an output indicative of said pressure, and voice synthesizer means responsive to the pressure detection means for synthesizing voice indicative of said pressure and generating the voice.

BRIEF DESCRIPTION OF THE DRAWINGS

The present invention will become more fully understood from the detailed description given hereinbelow and accompanying drawings which are given by way of illustration only, and thus are not limitative of the present invention and wherein.

DESCRIPTION OF THE INVENTION

Attention is directed to a first preferred embodiment of the present invention where an electronic sphygmomanometer is provided for speaking blood pressures each time a pressure to inflate an occluding cuff increases over a predetermined value.

When the occluding cuff is inflated to a pressure exceeding the patient's systolic pressure to close the artery, the pressure must exceed the assumed systolic pressure by about 3 mmHg. The sphygmomanometer of the invention speaks the blood pressures each time the pressure to inflate the cuff increases over a predetermined value, making operation of the apparatus easier.

Figure 1:
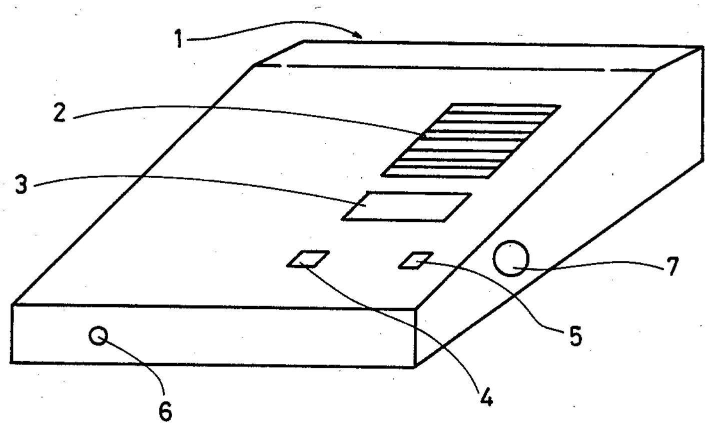
FIG. 1 shows a perspective view of an electronic sphygmomanometer according to the present invention.

FIG. 1 shows a perspective view of an electronic sphygmomanometer 1 according to the present invention. The sphygmomanometer 1 comprises a speaker 2, a display 3, a power switch 4, a repeat key 5, an earphone jack 6, and an adjuster knob 7.

Through the speaker 2, voice information representative of a blood pressure measured is spoken as one reads the display. The blood pressure, e.g., a systolic pressure and a diastolic pressure measured is displayed in the display 3. The power switch 4 is operated to control to power the sphygmomanometer 1.

The repeat key 5 is actuated to repeatedly speak the blood pressure of the systolic and diastolic pressures after the blood pressure has been measured and spoken. The speaker 2, the display 3, the power switch 4 and the repeat key 5 are disposed over the upper panel of the sphygmomanometer 1.

Earphones are coupled to the earphone jack 6 disposed on the front panel of the sphygmomanometer 1. The adjuster knob 7 is rotated to adjust a pressure-reduction rate. The adjuster knob 7 is disposed on the right side of the sphygmomanometer 1. Although not shown, a connector terminal is provided to which a pressure hose is connected to supply pressurized air. The connector terminal is disposed on the left side of the sphygmomanometer 1.

Figure 2:
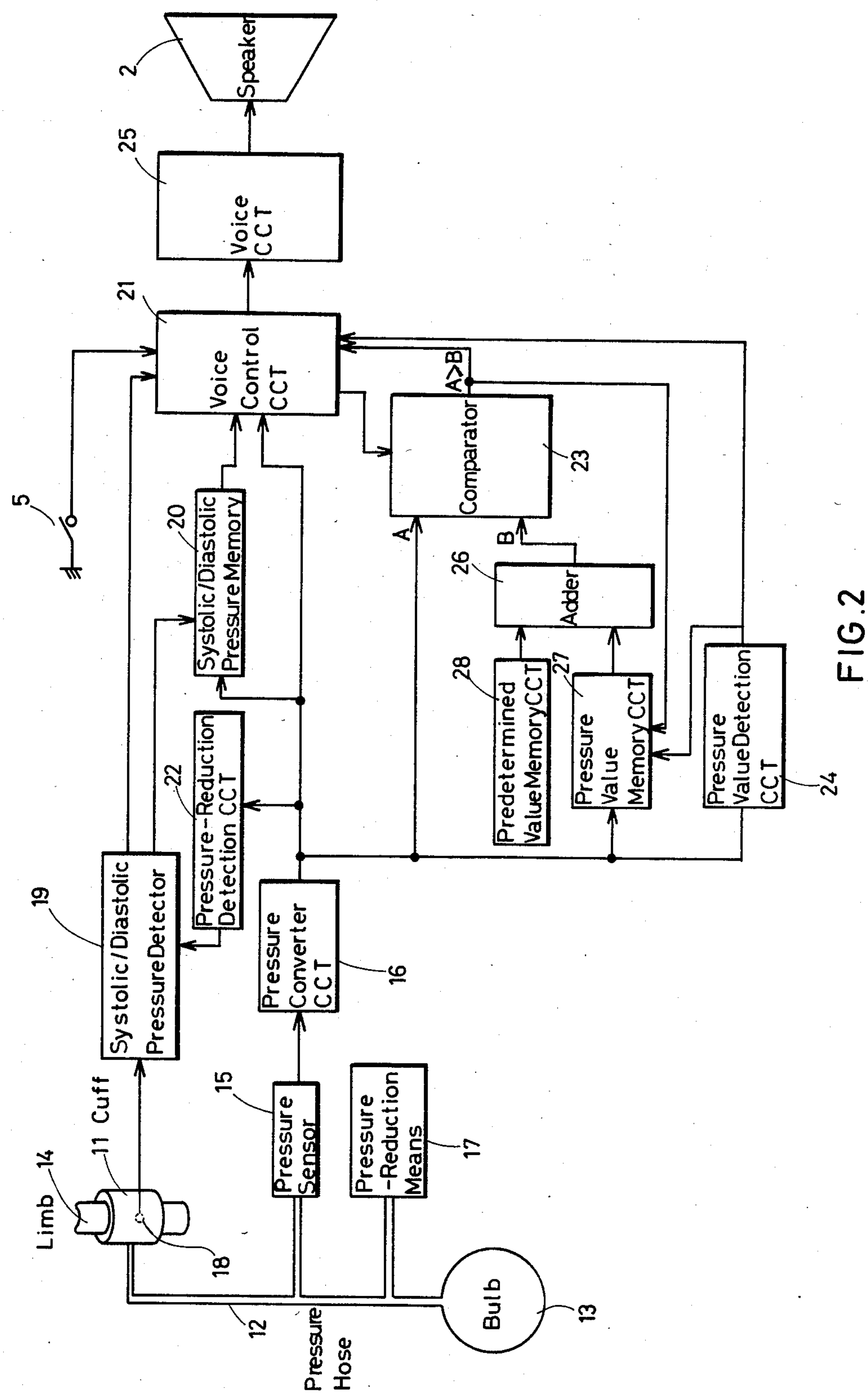
FIGS. 2, 4, 6, 7 and 9 show a block diagram of a circuit implemented within the sphygmomanometer of FIG. 1.

FIG. 2 shows a block diagram of a circuit implemented within the sphygmomanometer 1.

A patient's limb 14 is illustrated with the circuit of FIG. 2 which comprises an occulding cuff 11, a pressure hose 12, a bulb 13, a pressure sensor 15, a pressure converter circuit 16, a pressure-reduction means 17, a microphone 18, a systolic/diastolic pressure detector 19, a systolic/diastolic pressure memory 20, a voice control circuit 21, a pressure-reduction detection circuit 22, a comparator 23, a pressure value detection circuit 24, an adder 26, a pressure value memory circuit 27, a predetermined value memory circuit 28, a voice circuit 25, the aforestated speaker 2, and the repeat key 5.

The occluding cuff 11 is inflated by receiving a fluid, such as air, applied thereto by the pressure hose 12. The cuff 11 may be wrapped around the patient's limb 14 such as the upper arm to surround the brachial artery. Alternatively, the cuff may be wrapped around a patient wrist. Suitable fastening members, not shown, are used to maintain the cuff in a suitable position during inflation and deflation, and during pressure measurement.

The cuff 11 is manually inflated by squeezing the bulb 13. Fluid pulses are applied from the bulb 13 to the cuff 11 via the pressure hose 12. After inflation, the cuff 11 is adapted to be deflated.

The air pressure in the cuff 11 is forwarded via the air connector to the pressure sensor 15, so that the pressure sensor transduces the air pressure in the cuff 11 to electric analog signals. The pressure sensor 15 comprises a bellows for lengthening and shrinking responsive to an applied pressure, an oscillator, and a means for changing oscillation frequency developed from the oscillator according to the movement of the bellows.

The analog signals developed from the pressure sensor 15 are applied to the pressure converter circuit 16 so as to convert the analog signals into electrical digital signals representative of the cuff pressure.

The pressure-reduction means 17 is provided for reducing the cuff pressure, progressively. The means 17 comprises a needle valve for releasing the cuff pressure. A pressure-reduction rate by the means 17 is controlled by rotating the adjuster knob 7. The microphone 18 is provided within the cuff 11 for detecting the Korotkoff sounds. The Korotkoff sounds detected are entered into the systolic/diastolic pressure detector 19. The microphone 18 is of a ceramic piezoelectric type.

The systolic/diastolic pressure detector 19 determines the appearance and the disappearance of the Korotkoff sound, so that the pressures of the pressure converter circuit 16 at the time when the Korotkoff sound appears and disappears are taken as the systolic and the diastolic pressures. The systolic and the diastolic pressures are applied to and stored in the memory 20. Since the memory 20 detects that the pressures have been already measured, a measurement end signal is entered from the memory 20 to the voice control circuit 21.

The pressure-reduction detection circuit 22 is provided for detecting that the cuff 11 is being deflated, to measure the blood pressure. The detection output of the circuit 22 is inputted into the systolic/diastolic pressure detector 19 to enable the detector 19 to be operative.

The voice control circuit 21 is responsive to the systolic/diastolic pressure detector 19, the comparator 23, and the pressure value detection circuit 24 for enabling the voice circuit 25 to provide voice information representative of the systolic/diastolic pressure in the memory 20 and of the pressure converted by the pressure converter circuit 16. More particularly, the circuit 21 is responsive to the measurement end signal developed by the detector 19. The circuit 21 is responsive to the comparison output developed by the comparator 23. The detection circuit 24 detects the cuff pressure increase being over a predetermined value, e.g., about 20 mmHg to provide a detection signal. The circuit 21 is responsive to the detection signal developed by the detection circuit 24.

The voice circuit 25 comprises a ROM containing a plurality of items of voice information in many addresses for speaking many pressure values. The voice control circuit 21 is responsive to the applied pressure values for providing ROM address information for the circuit 25 corresponding to the values, and control signals, so as to control the circuit.

The voice circuit 25 comprises a voice synthesizer, the ROM for storing the voice information, and, if required, a power amplifier. The voice circuit 25 detects the ROM address information and the control signals developed from the voice control circuit 21 to address the voice information in the ROM.

The voice synthesizer is provided for synthesizing voice representative of the pressures using the voice information.

The synthesized voice is spoken through the speaker 2. The voice control circuit 21 generates a voice speaking completion signal for indicating that the voice output has been completed.

The voice speaking completion signal developed from the circuit 21 is inputted into the comparator 23. Responsive to this signal, the comparator 23 compares a pressure value A as outputted from the pressure converter circuit 16 and a pressure value B as outputted from the adder 26. When A>B, the comparator 23 develops an output signal indicative of A>B toward the voice control circuit 21 and the pressure value memory circuit 27.

Responsive to the output signal from the comparator 23, the pressure value memory circuit 27 renews its pressure contents to be outputted as voice. The predetermined value memory circuit 28 stores a predetermined pressure value, e.g., about 10 mmHg. The memory contents in the circuit 27 and 28 are added by the adder 26, so that the results are inputted into one input terminal of the comparator 23.

The pressure value detection circuit 24 detects the cuff pressure being over a predetermined value, e.g., about 20 mmHg. A detection output of the circuit 24 is applied to the pressure value memory circuit 27 and the voice control circuit 21. When output of the repeat key 5 is applied to the voice control circuit 21, responsive to the detection by the detection circuit 24 that the cuff pressure is over the predetermined value of about 20 mmHg, the detection output of the detection circuit 24 is read in again by the voice control circuit 21.

Figure 3:
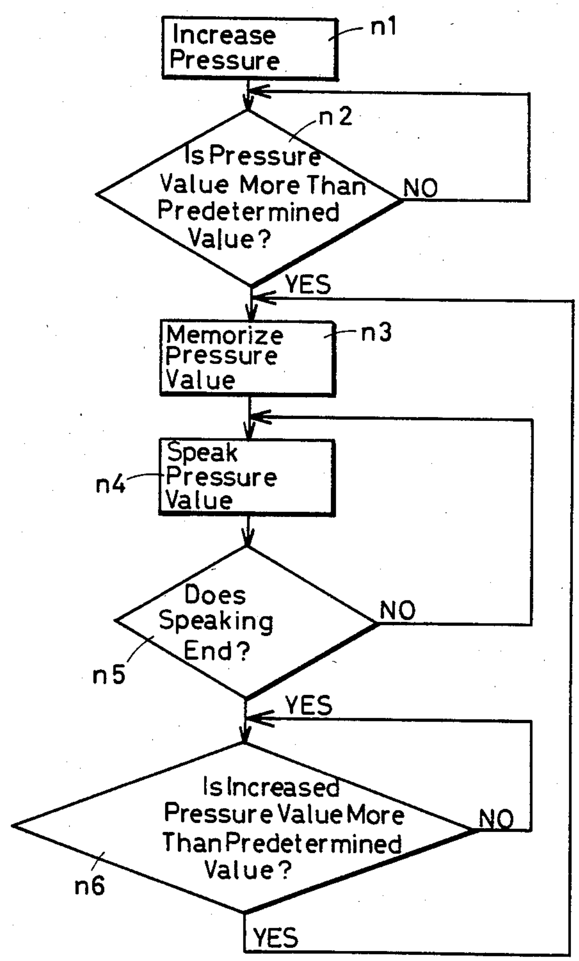
FIGS. 3, 5 and 8 show a flow chart of the operation of the sphygmomanometer as shown in FIG. 1.

FIG. 3 shows a flow chart of the operation of the circuit as shown in FIG. 2.

Step $n_1$ of FIG. 3:

The occluding cuff 11 is wrapped around the limb 14 after an air connector of the cuff 11 is coupled to the air connector terminal of the sphygmomanometer 1 via the pressure hose. The cuff 11 is inflated by squeezing the bulb 13 several times.

Step $n_2$ of FIG. 3:

The cuff pressure during the inflation is detected by the pressure sensor 15 to generate the electric analog signals. The converter circuit 16 converts the electrical analog signals into the digital signals. The digital signals are entered into the detection circuit 24 to determine whether the cuff pressure is over the predetermined value, e.g., about 20 mmHg.

Step $n_3$ of FIG. 3:

When the detection circuit 24 detects the cuff pressure being over the predetermined value, the circuit 24 outputs the detection signal. Responsive to this detection signal, the pressure value as outputted by the converter circuit 16 at this time is stored in the pressure value memory circuit 27.

Step $n_4$ of FIG. 3:

Further, the pressure value as outputted by the converter circuit 16 is inputted into the voice control circuit 21 to output the voice information and the control signals for the ROM of the voice circuit 25. The voice information represents the pressure value. The voice circuit 25 synthesizes voice as stated above. The speaker 2 provides the voice indicative of the pressure value.

Step $n_5$ of FIG. 3:

When the voice output has been completed, the voice control circuit 21 outputs the voice speaking completion signal.

Step $n_6$ of FIG. 3:

The voice speaking completion signal is applied to the comparator 23. The comparator 23 compares the pressure A as outputted from the converter circuit 16 and the pressure B as outputted from the adder 26. The pressure B as outputted from the adder 26 is obtained by adding the memory contents of the pressure value memory circuit 27 and the predetermined value (about 10 mmHg) as set in the predetermined value memory circuit 28. The memory circuit 27 stores a previous pressure which has just been outputted as voice by the voice circuit 25.

When A>B, the comparator 23 outputs the output signal toward the voice control circuit 21 and the pressure value memory circuit 27.

Step $n_3$ of FIG. 3:

This step is reselected to renew the contents of the memory circuit 27.

Step $n_4$ of FIG. 3:

This step is also reselected to enable the voice control circuit 21 to be operative. The pressure as presently outputted from the converter circuit 16 is inputted into the control circuit 21. The control circuit 21 is responsive to the pressure for controlling to operate the voice circuit 25 so as to output the pressure as voice, in the manner similar to the above description.

The above operations are repeated to repeatedly speak the cuff pressure once the pressure exceeds the predetermined value of about 20 mmHg during the inflation of the cuff 11.

Once the cuff pressure is spoken and, thereafter, the cuff pressure increases by the predetermined value of about 10 mmHg more than a previous cuff pressure which has just been outputted as voice, the increased cuff pressure is spoken, also.

Preferably, an operator can confirm that a present cuff pressure exceeds an assumed systolic pressure by some values, e.g., about 30 mmHg by referring to the voice outputs of the pressures.

After the cuff pressure exceeds an assumed systolic pressure by about 30–40 mmHg, the inflation operation of the cuff 11 stops and the pressure-reduction means 17 is operated to evacuate the air in the cuff 11 at a rate as controlled by the means 17. The pressure-reduction detection circuit 22 detects this deflation condition to output a signal toward the systolic/diastolic pressure detector 19.

The pressures are measured. The microcophone 18 detects the Korotkoff sound sometime after the cuff inflation stops. The sound detected is inputted into the systolic/diastolic presesure detector 19. The detector 19 assumes the pressure developed by the converter circuit 16 at the time when the Korotkoff sound is first detected to be the systolic pressure.

During the pressure deflation, the detector 19 detects the Korotkoff sound disappearing. The detector 19 assumes the pressure as developed by the converter circuit 16 at the time when the last Korotkoff sound is produced to be the diastolic pressure. The memory 20 stores the systolic and the diastolic pressures.

Responsive to the measurement end signal developed by the detector 19, the systolic and the diastolic pressures in the memory 20 are inputted into the voice control circuit 21. The voice information representative of the systolic and the diastolic pressure is synthesized by the voice circuit 25. This voice information is spoken by the speaker 2.

Attention is directed to another preferred embodiment of the present invention where the systolic and the diastolic pressures are outputted as voice.

Figure 4:
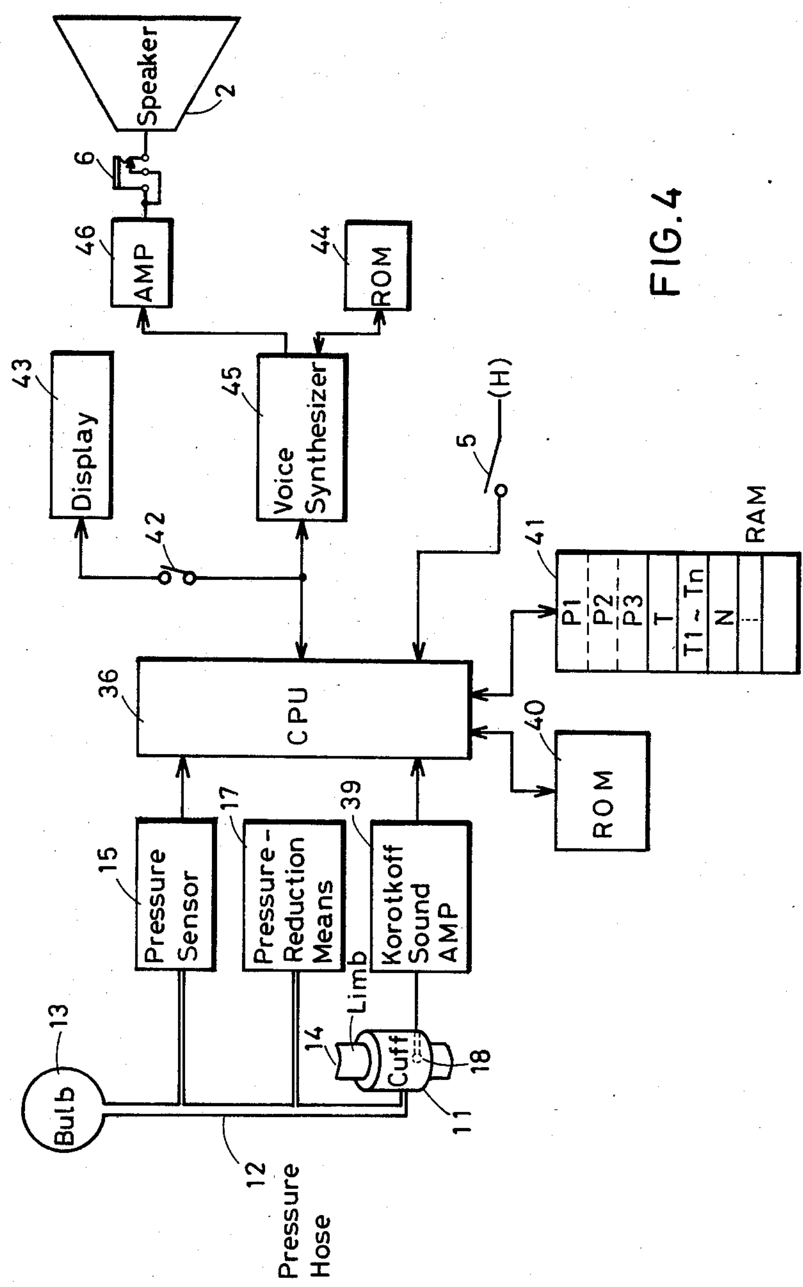

FIG. 4 shows a block diagram of a circuit of the sphygmomanometer 1 according to this preferred embodiment. The circuit of FIG. 4 is similar to that of FIG. 2 except that a CPU 36, a Korotkoff sound amplifier 39, a ROM 40, a RAM 41, a display switch 42, a display 43, a ROM 44, a voice synthesizer 45, and an amplifier 46 are connected in the circuit of FIG. 4.

The circuit of FIG. 4 is illustrated in a micro-computer version. Like elements corresponding to those of FIG. 2 are indicated by like numerals.

The CPU 16 receives the pressure output of the pressure sensor 15 to transduce the analog signals into the digital signals. The Korotkoff sound amplifier 39 amplifies the Korotkoff sounds detected by the microphone 18, so that the amplified sounds are inputted into the CPU 36.

Figure 5:
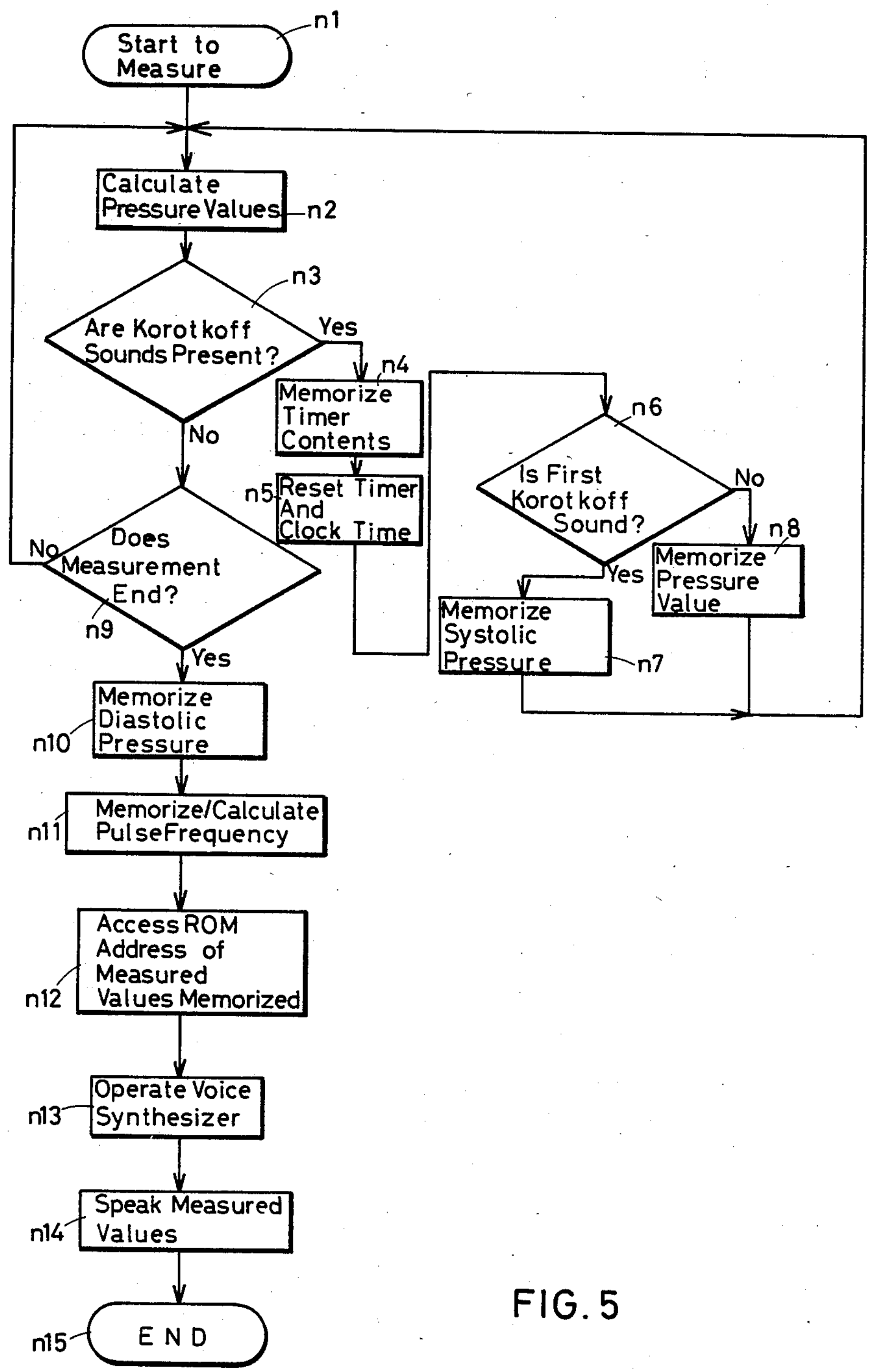

The CPU 36 is responsive to the control by the ROM 40 for calculating the pressures on the basis of the outputs of the pressure sensor 15 and the Korotkoff sound amplifier 39. Further, the CPU 36 detects the systolic pressure, the diastolic pressure and the pulse frequency, so as to store these measured data in locations $P_1$ to $P_3$ and N of the RAM 41. The ROM 40 stores a program operated as shown in FIG. 5.

The CPU 36 sends the measured data as stored in the RAM 41 toward the display 43 (related to the display 3 of FIG. 1) via the display switch 42.

After the CPU 36 detects the measurement completion, it changes the measured data in the RAM 41 into addresses for voice information as stored in the ROM 44. The CPU 36 inputs the voice information addresses and the control signals into the voice synthesizer 45. Responsive to the voice information addresses and the control signals, the voice synthesizer 45 synthesizes a voice based on the voice information in the ROM 44.

After amplification by the amplifier 46, the voice is spoken by the speaker 2. The earphone jack 6 is connected between the amplifier 46 and the speaker 2.

In operation, the cuff pressures during the inflation are detected by the pressure sensor 15 and the electrical analog signals are inputted into the CPU 36. The address information, for the ROM 44, corresponding to the pressures and the control signals are applied to the voice synthesizer 45, so that the synthesizer 45 makes the voice information. The voice information representative of the pressures during the inflation is spoken by the speaker 2.

FIG. 5 shows a flow chart of the operation of the circuit as shown in FIG. 4.

Step $n_1$ of FIG. 5:

The operator continues to inflate the cuff 11 until the cuff pressure exceeds an assumed systolic pressure by some value, e.g., about 30 mmHg, referring to the repeated voice outputs of the increasing pressures.

When the inflation operation is completed, the cuff 11 is deflated by operating the pressure-reduction means 17. The deflation operation is detected by the CPU 36 to start to measure the blood pressures.

Step $n_2$ of FIG. 5:

The pressures as detected by the pressure sensor 15 during the deflation are inputted into the CPU 36, for the CPU 36 to calculate the pressures as the digital signals.

Step $n_3$ of FIG. 5:

After the cuff inflation stops, the microphone 18 detects the Korotkoff sound which is to be amplified by the amplifier 39. The amplified sound is inputted into the CPU 36. The CPU 36 monitors the thus inputted Korotkoff sounds.

Step $4_4$ of FIG. 5:

By detecting the input of the Korotkoff sounds, the CPU 36 enables the clock contents of timer T in the RAM 41 to be stored in timer locations $T_1$–$T_n$ in the RAM 41.

Step $n_5$ of FIG. 5:

The clock contents of the timer T are reset and a next clocking operation of this timer T starts.

Step $n_6$ of FIG. 5:

The CPU 36 determines whether the inputted Korotkoff sound is the first such sound or not.

Step $n_7$ of FIG. 5:

When the first Korotkoff sound is detected, the CPU 36 forwards the present cuff pressure toward a location $P_1$ in the RAM 41. The location $P_1$ memorizes it as the systolic pressure.

Step $n_8$ of FIG. 5:

For subsequent Korotkoff sounds, the CPU 36 forwards the present cuff pressure toward a location $P_3$ in the RAM 41 for updating.

Step $n_2$ of FIG. 5 is reselected, so that the above steps are repeated, if necessary.

According to the above repeat operation, the timer T contains time intervals between input of the Korotkoff sounds. The time intervals in the timer T are sequentially stored in the locations $T_1$–$T_n$.

Step $n_9$ of FIG. 5:

When the CPU 36 detects no Korotkoff sounds being inputted in step $n_3$, step $n_9$ is selected to determine whether the pressure measurements are completed. More particularly, the CPU 36 determines whether the timer T contains a time more than a predetermined value, e.g., about 5 sec. When the time is less than this predetermined value, step $n_2$ is reselected. When the time is more than this predetermined value, the pressure measurement completion is detected to thereby select step $n_{10}$.

Step $n_{10}$ of FIG. 5:

A location $P_2$ in the RAM 41 stores a cuff pressure as stored in the location $P_3$ at the time when the last Korotkoff sound is detected, as the diastolic pressure.

Step $n_{11}$ of FIG. 5:

The pulse frequency is calculated, so that the pulse frequency is stored in the location N in the RAM 41. The CPU 36 calculates the pulse frequency from the time intervals of the Korotkoff sounds as stored in the locations $T_1$–$T_n$ in the RAM 41. For example, the pulse frequency is obtained by subtracting 60 from a median value (sec.) of the data in the locations $T_1$–$T_n$.

Step $n_{12}$ of FIG. 5:

The CPU 36 extracts the systolic pressure, the diastolic pressure, and the pulse frequency from the locations $P_1$, $P_2$ and N in the RAM 41, respectively. The CPU 36 determines the address information, so that the ROM 44 generates the voice information corresponding to the systolic pressure, the diastolic pressure and the pulse frequency as extracted by the CPU 36. The voice information and the control signals are inputted into the voice synthesizer 45.

Step $n_{13}$ of FIG. 5:

Responsive to the control signals and the address information generated by the CPU 36, the voice synthesizer 45 synthesizes voice for the systolic pressure, the diastolic pressure and the pulse frequency, by extracting the voice information from the ROM 44.

Step $n_{14}$ of FIG. 5:

The speaker 2 is operated to speak the systolic pressure, the diastolic pressure and the pulse frequency, sequentially.

Step $n_{15}$ of FIG. 5:

The blood pressure measurement is completed.

As stated above, when the CPU 36 detects the pressure measurement completion in step $n_9$, steps $n_{10}$–$n_{14}$ are selected to speak the systolic pressure, the diastolic pressure and the pulse frequency.

The display switch 42 is closed to forward the data for the systolic pressure, the diastolic pressure and the pulse frequency toward the display 43, so that they are displayed digitally in the display 43. When the display switch 42 is opened, these data are not displayed in the display 43.

When the earphones are connected to the earphone jack 6, the speaker 2 is prevented from operating. When the operator uses the earphones to hear the systolic pressure, the diastolic pressure and the pulse frequency, the patient is prevented from hearing these measured data.

Figure 6:
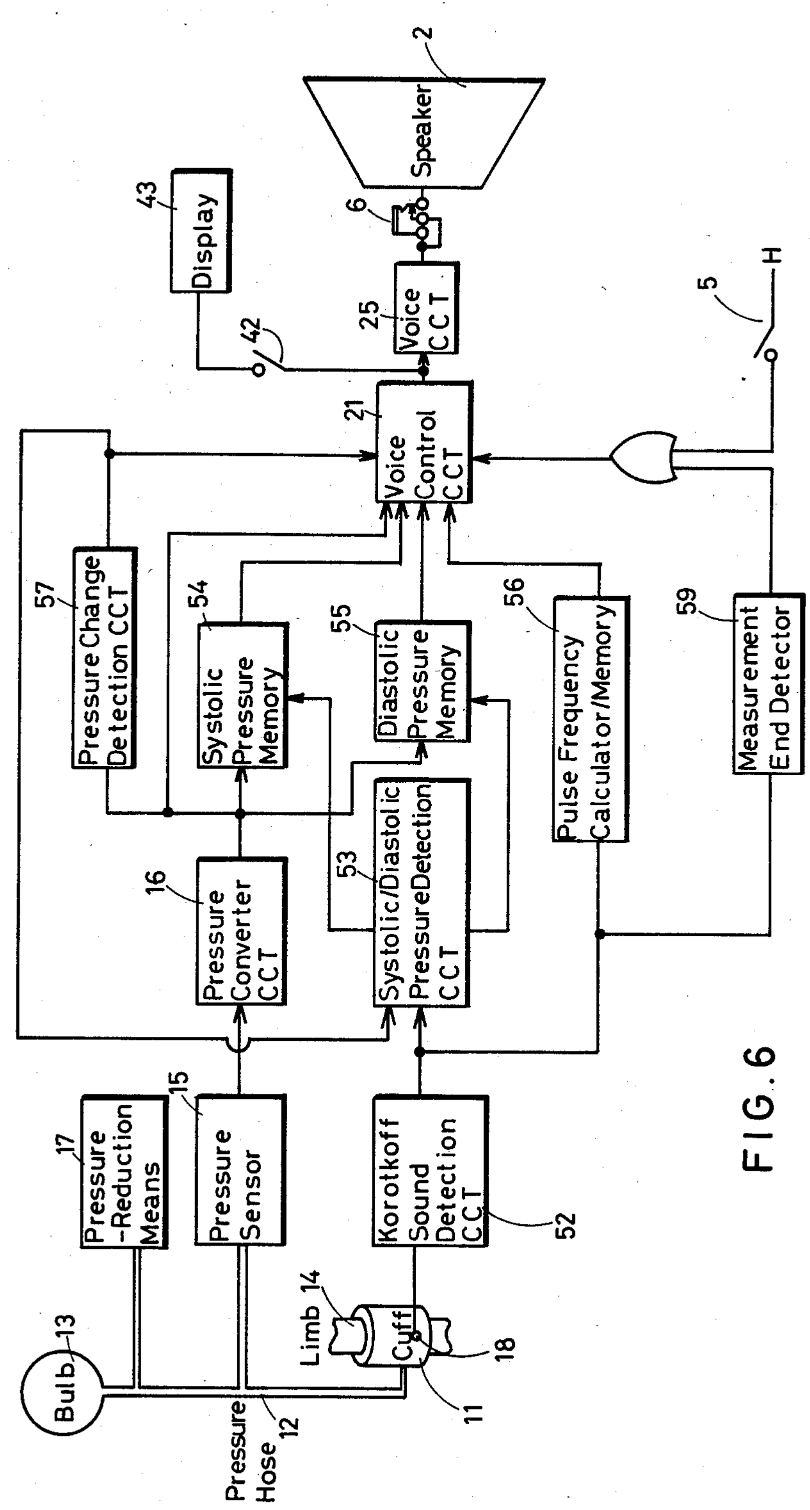

FIG. 6 shows another illustration of the circuit of FIG. 4, in a hardware version. The circuit diagram of FIG. 6 is similar to that of FIG. 4, basically, because the same purposes are achieved. Also, the circuit of FIG. 6 is similar to that of FIG. 2 since both are in the hardware version. Therefore, like elements corresponding to those of FIGS. 2 and 4 are illustrated by like numerals in FIG. 6.

Additionally and/or alternatively, the circuit of FIG. 6 comprises a Korotkoff sound detection circuit 52, a systolic/diastolic pressure detection circuit 53, a pressure change detection circuit 57, a systolic pressure memory 54, a diastolic pressure memory 55, a pulse frequency calculator/memory 56, and a measurement end detector 59.

The Korotkoff sound detection circuit 53 receives the output of the microphone 18 to detect the Korotkoff sounds. The Korotkoff sounds detected are inputted into the systolic/diastolic pressure detector circuit 53 for detecting the first generation and the last generation of the Korotkoff sounds. The detection circuit 53 selects the cuff pressures at times of the first and the last generations as developed from the pressure converter circuit 16 to be the systolic pressure and the diastolic pressure, respectively. The memories 54 and 55 store these pressures.

The pulse frequency calculator/memory 56 calculates the pulse frequency based on the time intervals of the Korotkoff sounds as outputted by the detection circuit 52 to store the results. The pressure change detection circuit 57 detects the inflation and the deflation operations of the cuff 11. The cuff pressures during the inflation operation are sent from the detection circuit 57 to the voice control circuit 21. The cuff pressures during the deflation operation are sent from the circuit 57 to the systolic/diastolic pressure detection circuit 53 to thereby operate this circuit 53.

The measurement end detector 59 detects the measurement end by determining whether the Korotkoff sounds are not detected by the detection circuit 52 for a predetermined time, e.g., about 5 sec. The measurement end signal is inputted from the detector 59 to the voice control circuit 21.

The voice control circuit 21 responds to the inflation operation condition detected by the detection circuit 57, the measurement end signal outputted by the detector 59, and the actuation signal of the repeat key 5. The voice control circuit 21 makes the control signals, and the address information for the ROM in the voice circuit 25 for storing the voice information, based on the data inputted thereto. The voice circuit 25 is operated to speak via the speaker 2 the cuff pressures converted by the converter circuit 16, and the systolic pressure, the diastolic pressure and the pulse frequency as stored, respectively, in the memories 54, 55 and 56.

Further attention is directed to a further preferred embodiment of the present invention where a sphygmomanometer is provided for speaking to inform an operator whether the sphygmomanometer can start a first measurement operation, and, if necessary, a subsequent measurement operation.

Preferably, the first measurement-possibility state should be spoken before the measurement. And, further, when the operator measures his blood pressures himself, preferably, the blood pressures should be measured after the cuff has been inflated and deflated once to stabilize the measured data. Therefore, it is desired for the sphygmomanometer to speak for the above purposes.

Figure 7:
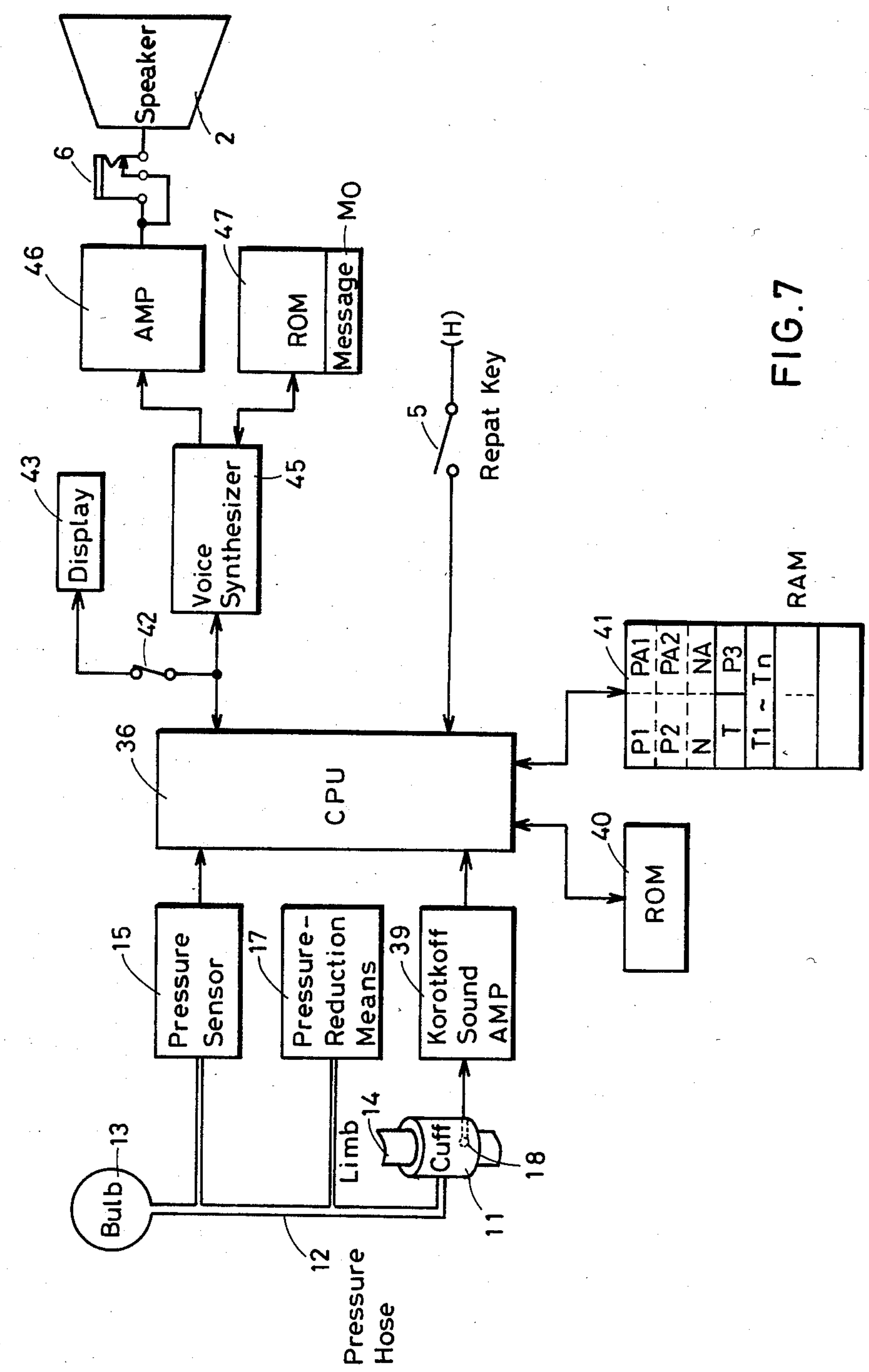

FIG. 7 shows a block diagram of a circuit of the sphygmomanometer 1 according to the further preferred embodiment.

The circuit of FIG. 7 is illustrated in the micro-computer version. The circuit of FIG. 7 is similar to that of FIG. 4 except that the ROM 44 of FIG. 4 is replaced by a ROM 47 containing a message in FIG. 7 and the RAM 41 in FIG. 7 is somewhat modified rather than the RAM 41 in FIG. 4.

The CPU 36 makes the address information corresponding to the measured data as stored in the RAM 41 as stated above. The address information is for the voice information stored in the ROM 47. The address information as composed by the CPU 36 is stored in locations $PA_1$, $PA_2$ and NA in the RAM 41.

The ROM 47 stores a plurality of items of the word information as stated above. Additionally, the ROM 47 contains a message location Mo for storing word information for a voice message equivalent to "New data can be measured." The CPU 36 detects next data being capable of being measured, so that the CPU 36 forwards the leading address information of the message location Mo toward the voice synthesizer 45.

The voice synthesizer 45 extracts the voice message information from the message location Mo of the ROM 47, to synthesize the voice message. The speaker 2 is operated to speak the voice message.

The CPU 36 receives the actuation signal of the repeat key 5.

Figure 8:
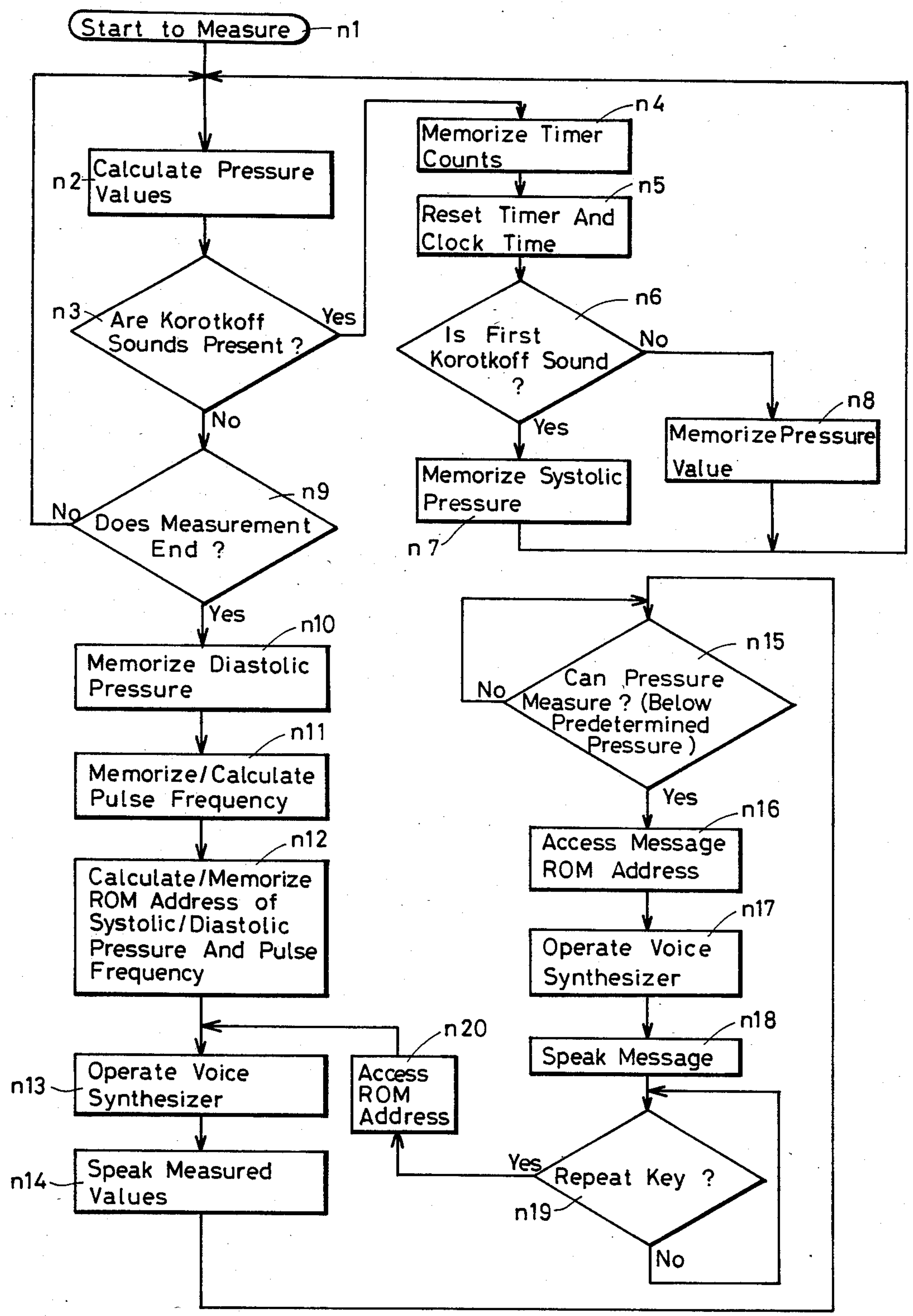

FIG. 8 shows a flow chart of the operation of the circuit as shown in FIG. 7. The flow chart of FIG. 8 is similar to that of FIG. 5 except that steps $n_{12}$, and $n_{15}$–$n_{20}$ are modified in the flow chart of FIG. 8 according to the operation of the circuit of FIG. 7.

Step $n_{12}$ of FIG. 8:

In addition to the operation effected in step $n_{12}$ of FIG. 5, the address information prepared by the CPU 36 for the ROM 47 is stored in the locations $PA_1$, $PA_2$ and NA of the RAM 41.

Step $n_{15}$ of FIG. 8:

After the pressures has been measured and the measured data have been spoken, the CPU 36 determines whether new pressure data can be measured because the cuff pressure is less than a predetermined value, e.g., about 20 mmHg.

Step $n_{16}$ of FIG. 8:

The CPU 36 outputs the leading address information of the message location Mo in the ROM 47 and the control signals toward the voice synthesizer 45.

Step $n_{17}$ of FIG. 8:

The voice synthesizer 45 is operated.

Step $n_{18}$ of FIG. 8:

Responsive to the address information and the control signals outputted by the CPU 36, the voice synthesizer 45 synthesizes the voice message based on the word information stored in the message location Mo of the ROM 47. The speaker 2 is operated to speak the voice message.

Step $n_{19}$ of FIG. 8:

When the repeat key 5 is closed between the measurement completion stage (or the measurement possibility stage) and a next-measurement start, the CPU 36 detects the repeat key 5 being operated.

Step $n_{20}$ of FIG. 8:

Responsive to the actuation signal of the repeat key 5, the CPU 36 generates the address information corresponding to the measured data stored in the location $PA_1$, $PA_2$ and NA of the RAM 41. The address information is to access the voice information from the ROM 47. The address information and the control signals are inputted into the voice synthesizer 45.

Steps $n_{13}$ and $n_{14}$ will be reselected, thereafter, to repeatedly speak the measured data.

Figure 9:
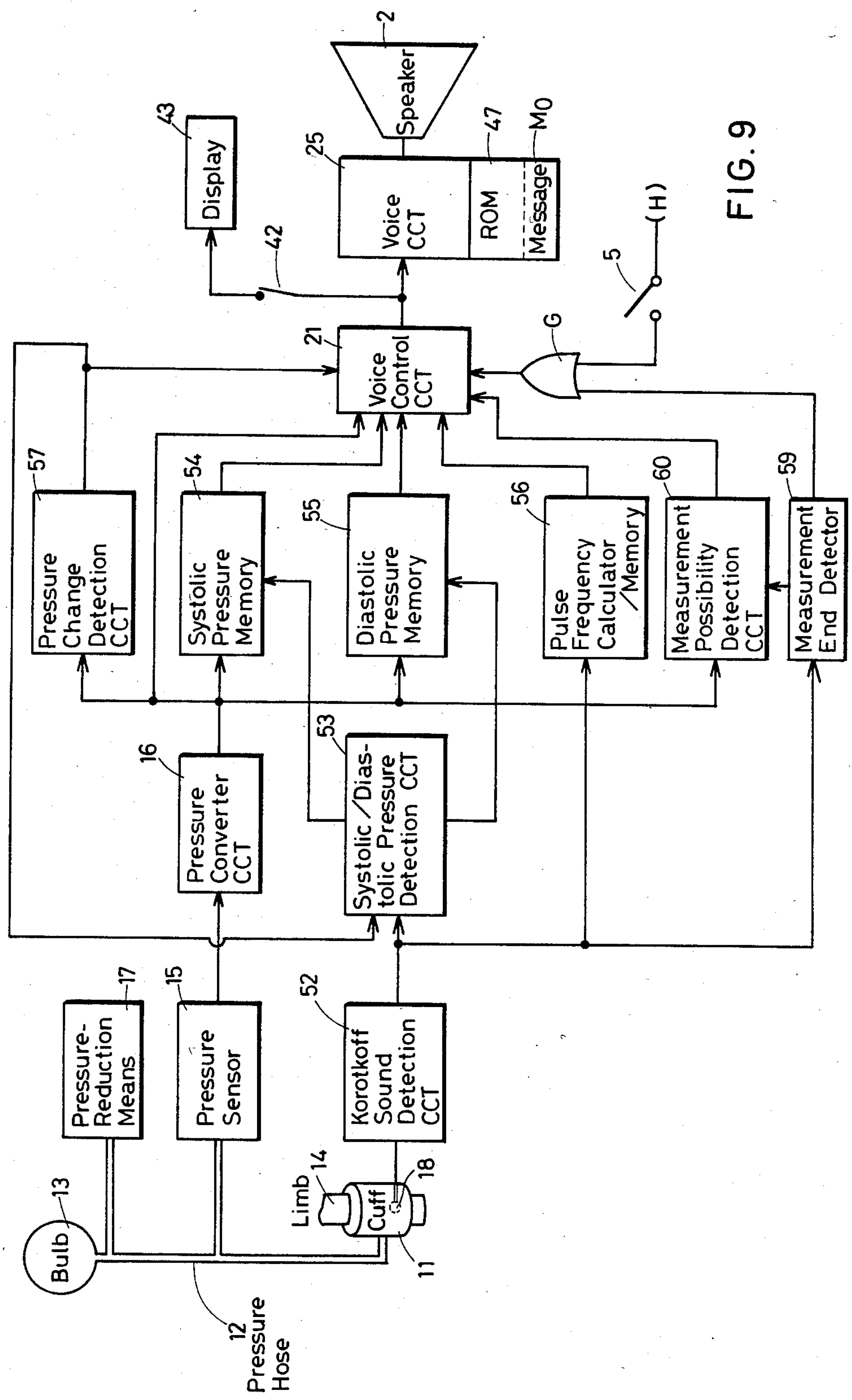

FIG. 9 shows another illustration of the circuit of FIG. 7, in the hardware version. The circuit diagram of FIG. 9 is similar to that of FIG. 7, basically, because the same purposes are achieved. Also, the circuit of FIG. 9 is similar to that of FIG. 6 since both are in the hardware version. Therefore, like elements corresponding to those of FIGS. 6 and 7 are illustrated by like numerals in FIG. 9.

The circuit of FIG. 9 is similar to that of FIG. 6 except that a measurement possibility detection circuit 60 is additionally connected in FIG. 9 and that the voice circuit 25 of FIG. 9 replaces the voice circuit 25 of FIG. 6.

The measurement possibility detection circuit 60 is responsive to the pressures outputted by the converter circuit 16 and the measurement end signal outputted by the measurement end detector 59 for determining whether new data can be measured because the cuff pressures is less than about 20 mmHg. The detection circuit 60 inputs a possibility-detection output into the voice control circuit 21.

The actuation signal of the repeat key 5 is inputted into the voice control circuit 21 via an OR gate G.

The voice control circuit 21 is responsive to the possibility-detection output generated by the detection circuit 60 for allowing the voice message to be spoken. The voice control circuit 21 generates the address information for the message location Mo of the ROM 47, and the control signals to start the voice circuit 25.

It may be possible that the detection circuit 60 is operated to speak the measurement possibility before the measurement operations are carried out.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A sphygmomanometer comprising:

pressure generating means for developing a variable pressure for facilitating measurement of systolic and diastolic pressure;

pressure detection means for measuring systolic and diastolic pressure and providing an output indicative of said pressures;

voice synthesizer means responsive to the pressure detection means for synthesizing audible voice output indicative of said systolic and diastolic pressures; and pressure increase detection means for detecting an increase in pressure in said pressure generating means, wherein said voice synthesizer means is responsive to said pressure increase detection means for generating periodic audible voice outputs indicative of the increasing pressure.

2. The sphygmomanometer of claim 1, further comprising means for detecting a pulse frequency operatively associated with said pressure detection means, said voice synthesizer means providing audible output of detected pulse frequency.

3. The sphygmomanometer of claim 1, further comprising means for initiating operation of the pressure increase detection means each time the pressure in said pressure generating means rises above a predetermined value.

4. The sphygmomanometer of claim 1, wherein the pressure increase detection means comprises means for determining whether a present pressure exceeds a previous pressure by a predetermined amount, said voice synthesizer means providing said periodic outputs each time a present pressure exceeds a previous pressure by said predetermined amount.

5. The sphygmomanometer of claim 1, further comprising readiness detection means responsive to the pressure detection means for detecting that said sphygmomanometer is ready to measure pressure.

6. The sphygmomanometer of claim 5, wherein the voice synthesizer means comprises means for storing a message indicating that the sphygmomanometer is ready to measure pressure, wherein said voice synthesizer means is responsive to said readiness detection means for audibly delivering said message.

7. The sphygmomanometer of claim 5, further comprising means for operating said readiness detection means before the pressure is to be measured by the pressure detection means.

8. The sphygmomanometer of claim 5, further comprising means for operating said readiness detection means after the pressure has been measured by the pressure detection means to indicate whether said sphygmomanometer is ready to again measure pressure.

9. The sphygmomanometer of claim 1, wherein said voice synthesizer means is responsive to said pressure increase detection means for generating audible voice output of said increasing pressure at predetermined pressure increments.

* * * * *